US009364544B2

(12) United States Patent
Pierre et al.

(10) Patent No.: US 9,364,544 B2
(45) Date of Patent: Jun. 14, 2016

(54) PHARMACEUTICAL COMPOSITIONS CONTAINING FUNCTIONALIZED TRIBLOCK COPOLYMERS

(71) Applicant: INGELL TECHNOLOGIES HOLDING B.V., Groningen (NL)

(72) Inventors: Sebastien Jerome Pierre, Maastricht (NL); Mike De Leeuw, Maastricht (NL)

(73) Assignee: Ingell Technologies Holding B.V., Groningen (NL)

( * ) Notice: Subject to any disclaimer, the term of this patent is extended or adjusted under 35 U.S.C. 154(b) by 0 days.

(21) Appl. No.: 14/853,181

(22) Filed: Sep. 14, 2015

(65) Prior Publication Data

US 2016/0000922 A1 Jan. 7, 2016

Related U.S. Application Data

(62) Division of application No. 13/520,966, filed as application No. PCT/EP2011/000041 on Jan. 7, 2011, now Pat. No. 9,168,221.

(30) Foreign Application Priority Data

Jan. 8, 2010 (EP) .................. 10000129.6

(51) Int. Cl.
*A61K 47/34* (2006.01)
*A61K 9/00* (2006.01)
*A61K 9/06* (2006.01)
*A61L 27/18* (2006.01)
*A61L 27/54* (2006.01)
*A61L 31/10* (2006.01)
*A61L 31/16* (2006.01)
*C08G 63/664* (2006.01)

(52) U.S. Cl.
CPC .............. *A61K 47/34* (2013.01); *A61K 9/0024* (2013.01); *A61K 9/06* (2013.01); *A61L 27/18* (2013.01); *A61L 27/54* (2013.01); *A61L 31/10* (2013.01); *A61L 31/16* (2013.01); *C08G 63/664* (2013.01); *A61L 2300/414* (2013.01)

(58) Field of Classification Search
CPC ....... A61K 9/0024; A61K 9/06; A61K 47/34; A61L 27/18; A61L 31/10
USPC ...................................... 514/772.1
See application file for complete search history.

(56) References Cited

U.S. PATENT DOCUMENTS

| 4,079,038 | A | 3/1978 | Choi et al. |
| 4,093,709 | A | 6/1978 | Choi et al. |
| 4,131,648 | A | 12/1978 | Choi et al. |
| 4,138,344 | A | 2/1979 | Choi et al. |
| 4,180,646 | A | 12/1979 | Choi et al. |
| 4,304,767 | A | 12/1981 | Heller et al. |
| 4,946,931 | A | 8/1990 | Heller et al. |
| 5,626,862 | A | 5/1997 | Brem et al. |
| 5,651,986 | A | 7/1997 | Brem et al. |
| 5,702,717 | A | 12/1997 | Cha et al. |
| 5,968,543 | A | 10/1999 | Heller et al. |
| 6,004,573 | A | 12/1999 | Rathi et al. |
| 6,117,949 | A | 9/2000 | Rathi et al. |
| 6,201,072 | B1 | 3/2001 | Rathi et al. |
| 2004/0106987 | A1 | 6/2004 | Palasis et al. |
| 2007/0014848 | A1 | 1/2007 | Buchholz et al. |
| 2007/0224236 | A1 | 9/2007 | Boden |
| 2007/0265356 | A1* | 11/2007 | Kim ................ A61K 9/0024 424/426 |

FOREIGN PATENT DOCUMENTS

| EP | 0558965 A2 | 9/1993 |
| EP | 0778304 A2 | 6/1997 |
| EP | 0863745 B1 | 9/1998 |
| WO | 0018821 | 4/2000 |

OTHER PUBLICATIONS

Lin Yu, Guangtao Chang, Huan Zhang, Jiandong Ding; Temperature-Induced Spontaneous Sol-Gel Transitions of Poly(D,L-lactic acid-co-glycolic acid)-b-Poly(ethylene glycol)-b-Poly(D,L-lactic acid-co-glycolic acid) Triblock Copolymers and Their End-Capped Derivatives in Water; Published online in Wiley InterScience (www.interscience.wiley.com), received Sep. 29, 2006; accepted Nov. 11, 2006, pp. 1122-1133.

Lin Yu, Huan Zhang, and Jiandong Ding; A Subtle End-Group on Macroscopic Physical Gelation of Triblock Copolymer Aqueous Solutions; Angew. Chem. Int. Ed. 2006, 45, 2232-2235; www.angewandte.org; Received Oct. 8, 2005; Revised Dec. 18, 2005; Published online: Mar. 3, 2006.

Lin Yu, Zheng Zhang, Huan Zhang, and Jiandong Ding; Mixing a Sol and a Precipitate of Block Copolymers with Different Block Ratios Leads to an Injectable Hydrogel; Biomacromolecules 2009, 10, 1547-1553; Published on Web Apr. 22, 2009.

Zhang et al., (Macromolecules, vol. 42, Issue 4, pp. 1010-1016, published on Web Jan. 26, 2009).

* cited by examiner

*Primary Examiner* — Johann R Richter
*Assistant Examiner* — Yanzhi Zhang
(74) *Attorney, Agent, or Firm* — Hudak, Shunk & Farine Co., LPA

(57) ABSTRACT

Amphiphilic triblock copolymers B-A-B, wherein A is a linear poly(ethylene glycol) block, having a number average molecular weight ($M_n$) of between 900 and 3000 Daltons, determined with size exclusion chromatography; wherein B are hydrophobic blocks with at least two cyclic monomers selected from the group consisting of glycolide, lactide, 1,3-dioxan-2-one, 5,5-dimethyl-1,3-dioxan-2-one, 1,4-dioxan-2-one, 1,4-dioxepan-2-one, 1,5-dioxepan-2-one, each B-block having a number average molecular weight ($M_n$) of between 400 and 2000 Daltons, determined with size exclusion chromatography; and wherein 25% to 100% of the polymer hydroxyl end-groups are covalently modified with at least one derivative of a $C_2$-$C_{20}$ fatty acid. The invention also relates to compositions with such polymers and the use thereof.

14 Claims, No Drawings

PHARMACEUTICAL COMPOSITIONS CONTAINING FUNCTIONALIZED TRIBLOCK COPOLYMERS

FIELD OF THE INVENTION

The present invention relates to amphiphilic triblock copolymers, compositions comprising the copolymers and at least one therapeutically active agent as well as implants comprising the copolymers.

BACKGROUND OF THE INVENTION

Controlled release of therapeutically active agents has become essential in treatments of humans and animals.

In recent years, a number of polymers fabricated into devices as microspheres, microcapsules, liposomes, strands and the like have been developed for this reason. The active agent is incorporated into the interior of the devices and is after administration to the human or animal body slowly released by different mechanisms. U.S. Pat. Nos. 4,079,038, 4,093,709, 4,131,648, 4,138,344, 4,180,646, 4,304,767, 4,946,931 and 5,968,543 disclose various types of polymers that may be used for the controlled delivery of active agents. The fabrication of such devices is in many cases cumbersome, expensive and may also suffer from irreproducibility in the release kinetics. Furthermore, in most cases an organic solvent is used which may have adverse effect on the therapeutic agent and there could also be residual solvent in the device, which in many cases is highly toxic. Moreover the administration of the solution or dispersion containing the devices is not patient friendly, due to the high viscosity of such solutions or dispersions. Further, such devices are not generally useful for the delivery of proteins that usually undergo a loss of activity during their incorporation into the solid polymer.

An important improvement was found in the use of amphiphilic copolymers, especially triblock copolymers BAB with poly(ethylene glycol) as the central hydrophilic block A and terminal hydrophobic blocks B, with polymer hydroxyl end-groups modified with fatty acid derivatives. Such copolymers may form micelles or thermo-reversible gels in aqueous solutions that may contain at least one therapeutically active agent.

Micelles of the amphiphilic copolymer have a number of useful attributes. For example when micelles having the correct size are used, which is usually below 40 nm, they will not extravasate in normal vasculature, but are able to extravasate in a tumor that normally has a leaky vasculature. Because of this it is possible to achieve a high concentration of antineoplastic agents in the tumor, without incurring excessive toxicity in normal tissues.

In addition to the usefulness as micelles in tumor targeting, micelles also find important applications in the solubilisation of highly water insoluble drugs, since such drugs may be incorporated in the hydrophobic core of the micelle.

The use of micelles in tumor targeting and solubilisation of highly water-insoluble drugs has been extensively described by V. P. Torchilin, "Structure and design of polymeric surfactant-based drug delivery systems", *J. Controlled Release* 73 (2001) 137-172, and by V. P. Torchilin, "Polymeric Immunomicelles: Carriers of choice for targeted delivery of water-insoluble pharmaceuticals", *Drug Delivery Technology*, 4 (2004) 30-39.

Micelles based on poly(ethylene glycol) and poly(D,L-lactic acid) have been investigated by J. Lee, "Incorporation and release behavior of hydrophobic drug in functionalized poly(D,L-lactide)-block poly(ethylene oxide) micelles" *J. Controlled Release*, 94 (2004) 323-335. Micelles based on poly(ethylene glycol) and poly(β-benzyl-L-aspartate) have been investigated by Kataoka, G. Kwon, "Block copolymer micelles for drug delivery: loading and release of doxorubicin" *J. Controlled Release*, 48 (1997) 195-201. Micelles based on poly(ethylene glycol) and poly(ortho ester) have been described by Toncheva et. al., "Use of block copolymers of poly(ortho esters) and poly(ethylene glycol) micellar carriers as potential tumor targeting systems", *J. Drug Targeting*, 11 (2003) 345-353.

It is also possible for the amphiphilic copolymers of the invention to form a so-called thermo-reversible gel in an aqueous solution. Such a copolymer solution has the peculiar property that at room temperature it is water-soluble and at the body temperature of 37° C. it becomes water-insoluble and forms a gel.

The composition containing the copolymer and the therapeutically active agent may be administered at room temperature as a low viscosity aqueous solution, using a small gauge needle, thus minimizing discomfort for the patient. Once at body temperature the composition will form a well-defined gel that will be localized at the desired site within the body. Further, such materials are also uniquely suited for use with a protein as the therapeutically active agent since the protein is simply dissolved in the same solution that contains the amphiphilic copolymer and the solution is injected, without affecting the properties of the protein.

The therapeutically active agent is slowly released by diffusion, or by a combination of diffusion and erosion, from the micelles or the thermogels made of amphiphilic copolymers. Ultimately, the amphiphilic copolymer has to fall apart into small fragments that can be metabolized or removed from the body.

Thermogels have been extensively investigated. The most extensively investigated thermo gelling polymer is poly(N-isopropyl acrylamide). This polymer is soluble in water below 32° C. and sharply precipitates as the temperature is raised above 32° C. This temperature is known as the lower critical solution temperature, or LCST. Thus, such a polymer could be injected at room temperature as a low viscosity solution using a small bore needle, and once in the tissues, it would precipitate, forming a well-defined depot. However, such polymers are non-degradable. Such polymers were extensively described by Hoffman, in L. C. Dong et. al., "Thermally reversible hydrogels: III. Immobilization of enzymes for feedback reaction control", *J. Controlled Release*, 4 (1986) 223-227.

Thermogels using poly(lactide-co-glycolide) copolymers as the hydrophobic segment and poly(ethylene glycol) as the hydrophilic segment have been extensively investigated and are described in a number of patents and publications: U.S. Pat. Nos. 5,702,717, 6,004,573, 6,117,949, 6,201,072 B1. G. Zentner, *J. Controlled Release*, 72 (2001) 203-215.

Thermogels using poly(L-lactide-co-ε-caprolactone) copolymers as the hydrophobic segment en poly(ethylene glycol) as the hydrophilic segment have been described in US 2007/0265356. This patent describes end group modification with aliphatic hydrocarbons, in particular $C_3$-$C_{18}$ aliphatic hydrocarbons.

In an article published in Angew. Chem. Int. Ed. 2006, 45, p 2232-2235, "A Subtle End-Group Effect on Macroscopic Physical Gelation of Triblock Copolymer Aqueous Solutions", BAB blockcopolymers having the blocks PLGA/PEG/PLGA are described. The PEG (i.e. polyethylene glycol A-block) is viewed as the hydrophilic block, the PLGA (i.e. poly(lactic acid-co-glycolic acid B-block) is the hydrophobic block. The article shows that end-groups to the BAB block are important. If the end-group is a hydrogen atom, a soluble system is prepared. If the end-groups are acetate or propionate a thermo reversible gel can be prepared (which gel exists at room temperature, i.e. 25° C.). If the end-groups are butyrate, the modified blockcopolymer precipitates in a region from 0° C. to 50° C. The extent of esterification (i.e. endcapping in the context of the mentioned article) was higher than 90% for all derivatives.

A disadvantage of triblock copolymers known in the prior art, is that it is difficult to obtain an optimal balance between the polymer's hydrophilicity and hydrophobicity while at least maintaining biodegradability. It is therefore difficult to obtain polymers with a good water solubility and the ability to retain (hydrophobic) therapeutically active agents.

Another disadvantage of triblock copolymers known in the prior art, is that the thermogels formed at body temperature are only able to deliver therapeutically active agents for a few days except very hydrophobic drugs like paclitaxel, due to very fast diffusion of the drug out of the gel mass.

Another disadvantage of triblock copolymers known in the prior art is, that the biodegradability is either very fast (in the order of days) or very slow (in the order of months). This makes these copolymers less suitable for controlled drug release applications in which a treatment in the order of a week or a few weeks, especially when the controlled release is largely determined by the degradation (erosion) of the gel instead of diffusion of the medicament out of the gel (which may be the case for very hydrophobic drugs)

SUMMARY OF THE INVENTION

It is an object of the present invention to provide triblock copolymers, which offer a variety of conditions which broaden the scope of therapeutically active agents which can be delivered in a controlled manner and which copolymers enable tuning the time required to degrade in the human or animal body. It is also an object of the present invention to provide triblock copolymers of which are biodegradable.

DETAILED DESCRIPTION OF THE INVENTION

This object is achieved by providing an amphiphilic triblock copolymer B-A-B, wherein A is a linear poly(ethylene glycol) block, having a number average molecular weight ($M_n$) of between 500 and 3000 Daltons, determined with size exclusion chromatography; wherein B are hydrophobic blocks comprising at least two cyclic monomers selected from the group consisting of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, chi.-diethylpropiolactone, ethylene carbonate, ethylene oxalate, 3-methyl-1,4-dioxane-2,5-dione, 3,3-diethyl-1,4-dioxan-2,5-dione, 6,8-dioxabicyclooctane-7-one, ε-propiolactone, γ-butyrolactone, δ-valerolactone, ε-decalactone, 3-methyl-1,4-dioxane-2,5-dione, 1,4-dioxane-2,5-dione, 2,5-diketomorpholine, α,α-diethylpropiolactone, γ-butyrolactone, 1,4-dioxepan-2-one, 1,5-dioxepan-2-one, 6,6-dimethyl-dioxepan-2-one, 6,8-dioxabicyclooctane-7-one, 5,5-dimethyl-1,3-dioxan-2-one, each B-block having a number average molecular weight ($M_n$) of between 400 and 3000 Daltons, determined with size exclusion chromatography; and wherein 25% to 100% of the polymer hydroxyl end-groups are covalently modified with at least one derivative of a $C_2$-$C_{20}$ fatty acid and wherein the B-block does not include the combination of glycolide and lactide and not the combination of lactide and ε-caprolactone.

In one embodiment the invention relates to an amphiphilic triblock copolymer B-A-B, wherein A is a linear poly(ethylene glycol) block, having a number average molecular weight ($M_n$) of between 900 and 3000 Daltons, determined with size exclusion chromatography; wherein B are hydrophobic blocks comprising at least two cyclic monomers selected from the group consisting of glycolide, lactide, ε-caprolactone, 1,3-dioxan-2-one, 5,5-dimethyl-1,3-dioxan-2-one, 1,4-dioxan-2-one, 1,4-dioxepan-2-one, 1,5-dioxepan-2-one, each B-block having a number average molecular weight ($M_n$) of between 400 and 2000 Daltons, determined with size exclusion chromatography; and wherein 25% to 100% of the polymer hydroxyl end-groups are covalently modified with at least one derivative of a $C_2$-$C_{20}$ fatty acid, and wherein the B-block does not include the combination of glycolide and lactide and not the combination of lactide and ε-caprolactone.

The polymers of the present invention are designed to broaden the scope of therapeutically active agents which can be delivered in a controlled manner and to tune the time required to degrade in the human or animal body in such a way that full degradation is obtained shortly after full drug release.

The block ratio, in the context of the present invention, is the ratio between the sum of the number average molecular weights ($M_n$) of both hydrophobic blocks without counting the end group modification (the sum of the two B blocks) and the polyethylene glycol A-block.

The block ratio should be high enough to ensure that micelles or gels can be formed when dissolving the triblock copolymers in aqueous solutions, but low enough so that the copolymers do not start to precipitate in these aqueous solutions.

The required block ratio also depends on the hydrophobic block composition (i.e. B-blocks), and the degree of modification and nature of the fatty acid derivative used for end group modification.

Solubility of the triblock copolymers is tightly linked to the hydrophobicity of the polyester blocks. The more hydrophobic the polyester is, the lower the block ratio may be.

End group modification also influences the solubility of the triblock copolymers according to the present invention. Longer fatty acids will render the triblock copolymers more hydrophobic, and as a result, the block ratio will have to decrease to maintain solubility in aqueous solutions. The degree of modification of end-groups will also affect solubility. A triblock according to the present invention modified at 100% with a fatty acid will be more hydrophobic than the same triblock copolymer modified at 50% with the same fatty acid, so the block ratio will have to be lower with the fully modified copolymer to reach the same solubility in aqueous solutions.

In an embodiment, the block ratio, which is defined as the ratio between the sum of the number average molecular weight of the B-blocks and the number average molecular weight of the A-block, ranges between 0.5 and 3, preferably between 0.5 and 1.7, more preferably between 0.6 and 1.5, even more preferably between 0.7 and 1.3.

A-Block

The A-block in the triblock copolymer may be a linear poly(ethylene glycol) with a number average molecular weight which ranges between 500 and 3000 Daltons, or between 900 and 2500 Daltons.

Poly(ethylene glycol) is a diol also known as poly(ethylene oxide) and both names can be used interchangeably for the purpose of this invention.

B-Block

The B-blocks in the triblock copolymer may be hydrophobic blocks made by ring-opening polymerization of 2 or more cyclic monomers and with a number average molecular weight ranges between 400 and 3000 Daltons. Preferably the number average molecular weight of each B-block ranges between 450 and 2000 Dalton, more preferably between 500 and 1500 Dalton.

Cyclic monomers used to make B blocks are selected from the group consisting of glycolide, lactide, ϵ-caprolactone, p-dioxanone (1,4-dioxan-2-one), trimethylene carbonate (1,3-dioxan-2-one), 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, chi.-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, β-propiolactone, γ-butyrolactone, δ-valerolactone, ϵ-decalactone, 3-methyl-1,4-dioxane-2,5-dione, 1,4-dioxane-2,5-dione, 2,5-diketomorpholine, α,α-diethylpropiolactone, γ-butyrolactone, 1,4-dioxepan-2-one, 1,5-dioxepan-2-one, 6,6-dimethyl-dioxepan-2-one, 6,8-dioxabicycloctane-7-one, 5,5-dimethyl-1,3-dioxan-2-one, or preferably of the group consisting of glycolide, lactide, ϵ-caprolactone, 1,3-dioxan-2-one (also known as trimethylene carbonate), 5,5-dimethyl-1,3-dioxan-2-one, 1,4-dioxan-2-one, 1,4-dioxepan-2-one, 1,5-dioxepan-2-one, and wherein the B-block does not include the combination of glycolide and lactide and not the combination of lactide and ϵ-caprolactone.

Hydrophobic blocks containing the monomeric units described above mainly contain ester and/or carbonate bonds, making them easily biodegradable. They can be prepared in a range of well-defined molecular weights. This enables the fabrication of triblock copolymers that have a well-defined structure, so that well-defined micelles or thermogels can be formed from the copolymers and moreover good reproducibility in the release kinetics of the therapeutically active agent may be achieved.

The choice of monomers is based primarily on the rate and profile of biodegradation that one wants to achieve with the triblock copolymer in vivo. Polyesters made by combining these monomers have been studied for a while and some of the combinations are well known.

In most cases, the combinations involve only 2 monomers, although there are examples with 3 monomers in rare cases.

Biodegradation in the context of the present invention is assessed by the macroscopic disappearance of the polymer under its shape in the body (gel, thermogel, micelles).

The degradation of the polyesters blocks down to monomeric residues is not something that can be easily followed in vivo, and it usually takes longer to occur. It can be assessed in vitro by various analytical techniques including size-exclusion chromatography, nuclear magnetic resonance, MALDI-TOF, high pressure liquid chromatography and combinations of those.

The polyester combinations described below are chosen based on theoretical degradation in vitro. The biodegradation in vivo will usually be faster since a simple hydrolysis of the ester bond between the polyester blocks and the polyethylene glycol block will result in a severe disturbance of the macroscopic state of the polymer (gel, thermogel, micelle).

In an embodiment B-blocks comprise monomer combinations comprising between 50 and 100 mol % glycolide. Such B-blocks will be among the fastest to biodegrade. Preferably B-blocks comprise between 60 and 95 mol % glycolide, more preferably between 75 and 90 mol %. Combinations of glycolide with other monomers will result in tunable biodegradability. For example the time to degrade will increase in the range glycolide-lactide, glycolide-trimethylene carbonate and glycolide-caprolacton.

In an embodiment B-blocks comprise monomer combinations including between 50 and 100 mol %, preferably between 60 and 95 mol %, more preferably between 75 and 90 mol % lactide. Such combinations will also degrade relatively fast, but slower than the ones with equivalent amounts of glycolide. The time to degrade will also depend on whether racemic lactide or L-lactide is used. The higher crystallinity of L-lactide usually yields polyesters which take longer to degrade, longer than with racemic lactide. Such polymers will take a few weeks to degrade.

In an embodiment B-blocks comprise monomer combinations comprising between 50 and 100 mol %, preferably between 60 and 95 mol %, more preferably between 75 and 90 mol % trimethylene carbonate. Such combinations usually exhibit very slow biodegradation with the exception of lactide-trimethylene carbonate and glycolide-trimethylene carbonate. The resulting polyesters also contain carbonate bonds, giving them an amorphous state which tends to favor erosion-based biodegradation over bulk biodegradation, prolonging the macroscopic state of a gel, thermogel or micelle when compared with polymers degrading through bulk erosion (typically the ones based on lactide-glycolide polyesters). In the case of drug delivery, this makes it easier to control the delivery rate. These polyesters take at least 3 months to degrade, and triblock copolymers made from these at least 2 months.

In an embodiment B-blocks comprise monomer combinations comprising between 50 and 100 mol %, preferably between 60 and 95 mol %, more preferably between 75 and 90 mol % 5,5-dimethyl-1,3-dioxan-2-one (also called 5,5-dimethyl trimethylene carbonate) Such combinations will exhibit even slower degradation than with trimethylene carbonate, while still providing polyesters containing carbonate bonds to have amorphous properties, beneficial for erosion-based biodegradation. These polyesters take at least 4 months to degrade, and triblock copolymers made from these at least 3 months.

Other combinations of the listed monomers are also possible, and the skilled person is able to choose them according to the polymer properties that they need for a specific application.

The hydrophobic-type monomers of the B-blocks can be categorized into groups according to relative degree of hydrophobicity. Relatively low hydrophobicity monomers are for example 1,4-dioxan-2-one, glycolide, 1,5-dioxepane-2-one. Relatively high hydrophobicity monomers include lactide, ϵ-caprolactone and 5,5-dimethyl-1,3-dioxan-2-one. In the case a triblock copolymer is desired which has a slow degradation profile, monomers are selected that have a rather high hydrophobicity and optionally the B-block has a higher molecular weight. In the case a triblock copolymer is desired which has a fast degradation profile, the B blocks are built from monomers having a low hydrophobicity (hydrophilic monomers).

In an embodiment one of the cyclic monomers of the B-blocks is selected from the group consisting of glycolide, lactide, ϵ-caprolactone and 1,3-dioxan-2-one. Preferably, one of the cyclic monomers of the B-blocks is lactide or ϵ-caprolactone. Preferred combinations of cyclic monomers in the B-blocks of the copolymers according to the present invention include but are not limited to:

glycolide and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.

lactide and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.

1,3-dioxan-2-one and a monomer of the group of 5,5-dimethyl-1,3-dioxan-2-one, 1,4-dioxan-2-one, 1,4-dioxepan-2-one, 1,5-dioxepan-2-one.

ε-caprolactone and a monomer of the group of 1,3-dioxan-2-one, 5,5-dimethyl-1,3-dioxan-2-one, 1,4-dioxan-2-one, 1,4-dioxepan-2-one, 1,5-dioxepan-2-one.

Preparation of B-A-B Triblock Copolymers

B-A-B triblock copolymers may be synthesized by ring-opening polymerization, or polycondensation reactions.

B blocks can be polymerized by using the cyclic monomers mentioned above in a ring-opening polymerization using the hydroxyl end-groups of poly(ethylene glycol) to initiate the polymerization. This is a very controlled and straightforward way of preparing triblocks in one step for people skilled in the art. Schemes and details for similar ring-opening polymerization reactions can be found in several patents or patent applications including and not limited to EP0863745 and WO0018821.

An alternative is to prepare B blocks separately by using ring-opening polymerization initiated with a short mono functional alcohol, and then coupling these B blocks with poly(ethylene glycol) in the presence of coupling agents like isocyanates. Coupling reactions may also be done after activation of functional end-groups with activating agents like carbonyl diimidazole, N-hydroxysuccinimide, para-nitrophenyl chloroformate, succinic anhydride and the like.

Preparing B blocks by polycondensation reactions using the open form of the cyclic monomers mentioned above, such as lactic acid, glycolic acid, epsilon-hydroxyhexanoic acid and the like is also possible. Nevertheless, obtaining well-defined blocks in terms of average molecular weight and end group functionality with polycondensation reactions is particularly difficult, even for someone skilled in the art.

Thus obtained triblock copolymers usually have hydroxyl moieties at both extremities. Without modification, only very specific triblocks will form thermo-reversible gels or micelles in aqueous solutions. In the present invention, these hydroxyl moieties are therefore modified with derivatives of natural-occurring fatty acids to achieve formation of gels or micelles while keeping the polymer water-soluble and biodegradable.

End Group Modification of B-A-B Triblock Copolymers

B-A-B triblocks are preferably partially or completely modified using the terminal hydroxyl group of the B blocks. Fatty acids include a selection ranging from 2 to 20, preferably 6-18 carbons, saturated or unsaturated, preferably with even numbers of carbons. Most fatty acids with an odd number of carbons are not naturally present in warm bodies and thus less desirable from a polymer biodegradation point of view. Fatty acids with more than 20 carbons are very hydrophobic solids, and yields water-insoluble polymers when used in the scope of this invention.

Preferably, the fatty acids derivatives used to modify the polymer hydroxyl end-groups are selected from the group consisting of derivatives of caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, eicosapentaenoic acid.

These naturally occurring fatty acids are easily degradable through the acetyl-coenzyme A cycle. Furthermore these acids have less risk of exhibiting toxicity in vivo in quantities used in the scope in the present invention. Some of them could have beneficial or detrimental biological activities though. A person skilled in the art would have to take the fatty acid choice into account, depending on the application and the location in the body.

Derivatives of fatty acids refer to fatty acids which may have been modified or activated to allow coupling reactions with the triblock copolymers hydroxyl end-groups.

Coupling fatty acids to the B-A-B triblock copolymers may involve the use of coupling agents like (but not limited to) isocyanates or the derivatisation of either the fatty acids or the polymer end-groups. Functional groups of the fatty acids or polymers can be activated to promote coupling by using activating agents like (but not limited to) carbonyl diimidazole, N-hydroxysuccinimide, para-nitrophenyl chloroformate, succinic anhydride. Direct derivatives of fatty acids like but not limited to acid chlorides, anhydrides, isocyanates can also be used, especially since some of them are readily commercially available.

These coupling methods are well known to the one skilled in the art.

In one embodiment of the invention terminal hydroxyl groups of the B blocks are modified with fatty acids having between 2 and 6 carbon atoms.

The degree of modification of the polymers hydroxyl end-groups is a numerical value which quantifies the percentage of hydroxyl end-groups that have been modified with fatty acids derivatives. A degree of modification of 100% means that both polymer extremities have been entirely modified. 50% means that half of the extremities (one out of two) have been modified. This value, as well as the triblock average molecular weight, is preferably calculated using nuclear magnetic resonance, since it is one of the few analytical methods giving access to absolute numerical values, as opposed to analytical methods like size-exclusion chromatography, where the average-molecular weight is a value which is relative to a polymer standard such as polystyrene.

The optimal degree of modification which makes the polymers in this present invention able to form micelles or thermogels in aqueous solutions is dependent on various factors such as triblock average molecular weight, block ratio, monomer composition, nature of the fatty acids derivatives.

The hydrophobicity of the triblock copolymers according to the present invention will increase when the fatty acid derivatives is longer, for the same degree of end group modification.

The hydrophobicity of the triblock copolymers according to the present invention will increase when the degree of end-capping (i.e. end group modification) increases, for the same fatty acid derivatives.

To achieve solubility in aqueous solutions at a certain polymer concentration, as well as specific molecular assembly such as micelles or (thermo)gels, the fatty acid and the degree of end group modification should be chosen and tuned together with block length, block ratio and polyester block composition.

Modification with longer fatty acid derivatives will generally increase the degradation time of the polymer.

A triblock copolymer according to the present invention has two OH end-groups, which may be modified. A statistical distribution of molecules having 0, 1 or 2 modified end-groups will result in a degree of modification other then 100%, for example 60%. Various polymer purification methods can allow a person skilled in the art to narrow this distribution of polymer chains by separating polymer chains which are not modified (0%), half modified (50%) or completely modified (100%). The issue is that these purification methods are time-consuming and often not applicable to polymer batches larger than 5 grams. Having polymers with degrees of modification other than 0, 50 or 100% can be necessary to achieve proper preparation of gels or micelles depending on the fatty acid derivative, the monomer composition and the polymer block ratio and the polymer block size.

In the scope of the present invention, the numerical range for the degree of modification is between 25 and 100%, preferably between 40% and 98%, more preferably between 50 and 95%. The ranges are derived from experimental results with various fatty acids, monomer composition, block ratio and block size.

Triblock copolymers with degree of modification lower than 25% have been found to contain too much unmodified polymer chains to form thermogels in the solubility range that they have in aqueous solutions.

In a preferred embodiment at least 90% of the polymer hydroxyl end-groups of a polymer according to the present invention are covalently modified with at least one derivative of a $C_2$-$C_{20}$ fatty acid.

In this embodiment the degree of end group modification is thus at least 90%.

Such modified triblock copolymers provide a well defined structure and easily fold into U-shapes which assemble to form micelles with hydrophobic cores and hydrophilic shells in aqueous solutions.

In an embodiment, the block copolymer with the general formula B-A-B comprises poly(ethylene glycol) (PEG) as A-block, having a number average molecular weight of between 1000 and 2500 Dalton, preferably between 1100 and 2000 Dalton, determined with Size Exclusion Chromatography (SEC). The B-blocks are hydrophobic blocks comprising at least two cyclic monomers selected from the group consisting of glycolide, lactide, 1,3-dioxan-2-one (also known as trimethylene carbonate), 5,5-dimethyl-1,3-dioxan-2-one, 1,4-dioxan-2-one, 1,4-dioxepan-2-one, 1,5-dioxepan-2-one, each B-block having a number average molecular weight of between 400 and 1600 Dalton, preferably between 500 and 1500, more preferably between 600 and 1300 Dalton, determined with Size Exclusion Chromatography (SEC), wherein the B-block does not include the combination of glycolide and lactide.

In one embodiment the invention relates to an amphiphilic triblock copolymer B-A-B, comprising poly(ethylene glycol) (PEG) as A-block having a number average molecular weight of between 1000 and 2500 Dalton, determined with Size Exclusion Chromatography (SEC); the B-blocks being hydrophobic blocks comprising at least two cyclic monomers selected from the group consisting of glycolide, lactide, 1,3-dioxan-2-one, 5,5-dimethyl-1,3-dioxan-2-one, 1,4-dioxan-2-one, 1,4-dioxepan-2-one, 1,5-dioxepan-2-one, each B-block having a number average molecular weight of between 400 and 2500, determined with Size Exclusion Chromatography (SEC); wherein the amphiphilic triblock copolymer has a block ratio, defined as the ratio between the sum of the number average molecular weight of the B-blocks and the number average molecular weight of the A-block, of between 0.5 and 2.5; and wherein 25% to 100% of the hydroxyl endgroups are covalently modified with at least one derivative of a $C_2$-$C_{20}$ fatty acid derivatives, the fatty acids being selected from the group consisting of derivatives of acetic acid, butyric acid, caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, eicosapentaenoic acid; and wherein the B-block does not include the combination of glycolide and lactide.

The block ratio, defined as the ratio between the sum of the number average molecular weight of the B-blocks and the number average molecular weight of the A-block, ranges between 0.5 and 3, or between 0.5 and 2.5, preferably between 0.6 and 2.2, more preferably between 0.7 and 1.7. In this embodiment 25% to 100% of the hydroxyl endgroups are covalently modified with at least one derivative of a $C_2$-$C_{20}$, preferably $C_6$-$C_{18}$ fatty acid derivatives. In this embodiment, the fatty acids derivatives used to modify the polymer hydroxyl end-groups are preferably selected from the group consisting of derivatives of acetic acid, butyric acid, caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, eicosapentaenoic acid.

Biodegradation in the context of the present invention refers to the degradation, disassembly, digestion or disappearance of the amphiphilic copolymers by action of the biological environment, including action of living organisms and most notably at physiological pH and temperature. A principal mechanism for biodegradation in the present invention is the hydrolysis of linkages between and within the monomer units of the amphiphilic copolymers. Specific reactions include but are not limited to ester hydrolysis (chemical or enzymatic) and degradation of fatty acid fragments via lipolysis or oxidation.

Polymers of the present invention may be solubilised in aqueous solutions with concentrations preferably ranges between 3 and 50% by weight of the polymer. The most preferable concentrations to achieve thermogelation of formation of micelles are dependent on the polymer composition. Addition of therapeutically active agents to a polymer solution usually affects the optimal concentration to form micelles or thermogels, wherever the agents are dissolved, emulsified or suspended.

The invention also relates to compositions comprising at least one amphiphilic triblock copolymer of the present invention and a medically accepted solvent. A medically accepted solvent may be for example water; a mixture of water and an organic solvent like for example ethanol, isopropanol and DMSO; an isotonic aqueous solution which is suitable for injection in the human or animal body (i.e. in the context of the present invention a solution having an osmotic pressure comparable or at least compatible with the osmotic pressure of human or animal bodily fluids, like blood); benzylbenzoate and isopropyl myristate.

In an embodiment, such a composition comprises at least one therapeutically active agent and is a pharmaceutical composition.

By therapeutically active agents people skilled in the art refer to any set of molecules, cells or cell materials able to prevent, slow down, moderate or cure a disease in, or that can deliver a desired therapeutic effect on, a treated human or animal. Human diseases are referred to as defined by the World Health Organization in the WHO ICD-10 (2007) classification document.

Therapeutically active agents include but are not limited to nutrients, pharmaceuticals (small molecular entities), proteins and peptides, vaccines, genetic materials, (such as polynucleotides, oligonucleotides, plasmids, DNA and RNA), diagnostic agents, imaging agents, enzymes, nucleic acid sequences, antigens, antibodies, antibody fragments, viruses, virus-based materials, cells, cell substructures, growth factors, antibiotics, anti-inflammatory compounds, immune-modulating, anti-thrombogenic compounds, anti-claudicating drugs, anti-arrhythmic drugs, anti-atherosclerotic drugs, antihistamines, cancer drugs, vascular drugs, ophthalmic drugs, amino acids, vitamins, hormones, neurotransmitters, neurohormones, enzymes, signaling molecules, psychoactive medicaments, synthetic drugs, semi-synthetic drugs, natural drugs and substances derived from these, or combinations of the above.

The active pharmaceutical ingredient (API), may demonstrate any kind of activity, depending on the intended use. The active agent may be capable of stimulating, blocking or suppressing a biological response.

The therapeutic active agents can be used for sustained delivery in many different diseases and conditions within humans and animal.

In an embodiment the therapeutically active agent is a growth factor. Such a composition is very suitable for application in orthopedics and in particular in the prevention or treatment of diseases of intervertebral discs. This is because the composition will gel and hold the active agent in place over a period in time, releasing it in a controlled manner than straight injection of a non-gelling solution. Furthermore, the gel-forming polymers will be completely broken down after having completed their function. This is especially important in the application in the area of intervertebral discs, where there is less metabolic activity.

Preferably as growth factor at least one compound is used of the group consisting of transforming growth factor beta-3, osteogenic protein 1, bone morphogenic protein 2 and 7. Although less preferred it is also possible to use compositions containing thermogels in general and a transforming growth factor. Such a composition at least has the advantage of the slow release of the growth factor.

In yet another embodiment the therapeutic active agent is an agent to suppress or slow down cancerous growth or neovascularisation, such as anti-VEGF agents, si-RNA or aptamers.

In still another embodiment the therapeutic active agent is an agent to avoid, control, suppress, or eradicate infectious diseases.

The copolymers of the present invention will find utility in any of the uses for which biodegradable polymers are useful, including such uses as vehicles for the sustained and controlled release of therapeutically active agents, implants, tissue-engineering devices, and the like, they will also find particular utility in applications where their nature as block copolymers having both hydrophilic and hydrophobic segments confers a special benefit, and those uses will be addressed in greater detail below.

For some applications special moieties may have to be introduced into the fatty acid derivatives used for end group modification. For example, the use of unsaturated fatty acid may allow chemical reactions to occur between the unsaturated fatty acid chains to achieve polymer crosslinking. Crosslinking is usually carried out in order to modify the mechanical properties and degradation profile of polymers.

The activation and intermolecular reaction between those crosslinkable moieties is usually caused by a radiation source, an external chemical reaction or stimulus, or a combination thereof. Radiation examples include, but are not limited, to heat, infrared sources, ultra-violet sources, electron-beam sources, micro-waves sources, x-ray sources, visible light sources [monochromatic or not] and gamma-rays. External reaction, or stimulus include, but are not limited, to pH, oxidation/reduction reactions, reactions with a chemical agent present in vivo (gas, protein, enzymes, antibody etc), reaction with a chemical added to the composition upon introduction into the body, known as dual systems, for example a molecule containing two or more reactive groups.

Micellar Systems.

In one preferred embodiment a composition according to the present, the medically accepted solvent comprises water and the copolymer is present in a concentration above its critical micelle concentration (CMC), such that micelles are formed in an aqueous solution, the therapeutically active agent being entrapped in or controlled released by the micelles.

When the copolymers are placed in water, in which the hydrophilic segment is soluble and the hydrophobic segment is insoluble, the polymer chains may spontaneously self-aggregate to form micellar structures depending on their concentration.

One major utility of such micellar structures resides in their ability to entrap, controlled release and or solubilise hydrophobic drugs in the hydrophobic core of micelles. Such retention can be carried out in a number of ways. The drug may be added to the aqueous media containing the micelles and incorporated by simple stirring, by heating to moderate temperatures or by ultrasonification or by active loading as used in liposome production processes. Alternately, a drug dissolved in a volatile organic solvent is added to a water solution of preformed micelles with a subsequent solvent evaporation from the system.

While any of the anticancer agents that can be incorporated in micellar structures are suitable for this use, anticancer agents that are particularly suitable for micellar tumor targeting are those with low water solubility such as doxorubicin, daunorubicin, epirubicin, mitomicin C, paclitaxel, cis-platin, carboplatin, and the like. Other agents may include anticancer proteins such as neocarzinostatin, L-aspariginase, and the like and photosensitizers used in photodynamic therapy.

In addition to the usefulness as micelles in tumor targeting, micelles also find important applications in the solubilisation of highly water insoluble drugs, since such drugs may be incorporated in the hydrophobic core of the micelle.

Thermogels.

In another preferred embodiment a composition according to the present invention, the medically accepted solvent comprises water and the composition, being an aqueous solution, has a lower critical solution temperature (LCST) of between 4 and 37° C., such that the aqueous solution undergoes a sol-gel transition starting between 4 and 37° C.

Preferably, the composition also contains a therapeutically active agent.

The solution according to this embodiment has a lower critical solution temperature (LCST) below the warm body temperature (37° C. for a human body for example).

Such polymers are water-soluble below their LCST, also known as gel temperature, due to strong hydrogen bonding between the hydrophilic part of the chains and water, but above the LCST, hydrogen interactions are weakened and hydrophobic interactions between the hydrophobic domains of the polymer become dominant with consequent precipitation of the polymer, which can result in gelation of the polymer solution.

The LCST value depends on the balance of hydrophilic and hydrophobic portions of the block copolymer and can be adjusted by varying this balance. It also depends on the concentration of the block copolymer in the aqueous solution. Materials having particular usefulness for therapeutic applications are those where the LCST value is between 20 and warm body temperature since such materials will be soluble in aqueous solutions at room temperature and form a gel at body temperature (37° C. for a human body for example).

One of the desirable features of thermogels is the ability to administer thermogel formulations using a small bore needle resulting in significantly less pain on administration relative to the administration of microspheres, microcapsules, strands, or other solid drug-releasing devices. This is due to the water solubility of thermogels at room temperature, and the relatively low viscosity of the aqueous solution making the use of small-bore needles possible.

Another important and unique feature is the ability to deliver therapeutically active agents at a controlled rate and without loss of biological activity. In this application, the polymer according to the invention can be dissolved in an appropriate volume of an aqueous solution and the peptide, protein or nucleic acid sequence is dissolved in the same solution. The mixture is then injected in the desired body site, where it gels, entrapping the peptide, protein or nucleic acid sequence in the gelled material. It will be appreciated that these are extremely mild conditions since active agents are only exposed to water and at temperatures no higher than the warm body temperature.

This method is greatly superior to conventional methods of biomolecule incorporation into solid polymers that require harsh conditions such as elevated temperatures, and/or organic solvents, or mixtures of organic solvents and water and or surfactants, which usually results in loss of protein activity.

This method is particularly useful for the delivery and dosing of therapeutically active agents in applications including but not limited to injections of the thermogels containing the biomolecules mentioned above into articulate cartilage, pericardium, cardiac muscles, sclera and the vitreous body of the eye.

The LCST behavior also gives advantages when building composite devices. They can be built by using several thermogels with different LCST (always below warm body temperature). Upon implantation the in vitro degradation and release of actives can be tuned depending on their LCST and chemical structures.

The present invention further relates to applications of amphiphilic triblock copolymers according to the present invention and compositions thereof. In particular the present invention relates to medical devices comprising compositions comprising at least one amphiphilic triblock copolymer according to the present invention.

Medical Devices

Bio Erodible Copolymer. Matrix for Controlled Delivery and Tissue Engineering

The invention also relates to an implant containing the polymer according to the invention. In certain uses it is desirable to have a material that has improved mechanical properties relative to thermo gelling materials. To this effect, solid polymers can be prepared that are useful in a number of applications, for example orthopedic applications such as fracture fixation, or repair of osteochondral defects and the like. The solid polymer can be readily fabricated into a number of shapes and forms for implantation, insertion or placement on the body or into body cavities or passageways. For example, the block copolymer of this invention may be injection-molded, extruded or compression-molded into a thin film, or made into devices of various geometric shapes or forms such as flat, square, round, cylindrical, tubular, discs, rings and the like. Rod, or pellet-shaped devices may be implanted using a trocar, and these, or other shapes, may be implanted by minor surgical procedures. Alternatively, a device may be implanted following a major surgical procedure such as tumor removal in the surgical treatment of cancer. The implantation of polymer wafers containing anticancer agents is described for example, in Brem et. al., U.S. Pat. Nos. 5,626,862 and 5,651,986 and references cited therein; and the block and graft copolymers will find utility in such applications.

Tissue Engineering

Applications of tissue engineering devices comprising thermogels made with copolymers according to the present invention include but are not limited to nerve growth or repair, cartilage growth or repair, bone growth or repair, muscle growth or repair, skin growth or repair, secreting gland repair, ophtalmic repair. It should be underlined that thermogels may be used as such or as a part of a bigger implant, scaffold or structure.

Thermogel formulations with LCST below warm body temperatures may also be used as temporary void fillers in case of significant trauma, to prevent adhesion of damage tissues and scar tissue formation while waiting for corrective and reconstructive surgery. Void filling could be performed easily by injecting the thermogel formulation and removal could be performed via cutting, scraping or suction after cooling down the area to liquefy the thermogel. Other benefits of using void fillers may include but are not limited to: preventing contamination from outside, preventing infection, preventing surrounding tissue necrosis or alteration, inducing specific tissue formation (bone, cartilage, muscle, nerve, skin etc.), helping to maintain structural integrity of the surrounding tissues by itself or by combination with other known scaffolds or structures, trapping specific natural or foreign molecules.

Measurement Methods

The number average and weight average molecular weights ($M_n$ and $M_w$, respectively) of the triblock copolymers are determined with Size Exclusion Chromatography (SEC). Size-Exclusion Chromatography is performed with an Agilent 1100 series machine equipped with a thermostatically controlled double-C column system, in tetrahydrofuran at 25° C. Detection is done by refractive index measurement and UV. 50 micrograms of polymer solutions at 1 mg/ml are injected and runs lasted about 30 minutes. The external standards are series of polystyrene polymers. Relative values of the number average molecular weight $M_n$ and the weight average molecular weight $M_w$ can be obtained, as well as the polydispersity. The unit Daltons is equivalent to g/mol.

The molecular structure is determined with proton and carbon nuclear magnetic resonance ($^1$H NMR and $^{13}$C NMR, respectively), using deuterated chloroform (chloroform-d3) as solvent and reference.

Nuclear magnetic resonance is performed with a Brücker NMR Advance 300 (300 MHz) using chloroform-d3 as a solvent. Dimethylsulfoxide-d6 and deuterium oxide can be used in specific cases when polymer solubility in chloroform is too low. Samples concentration is about 10 mg/ml for a proton spectrum measurement and 20-30 mg/ml for a carbon spectrum measurement. For carbon measurement, DEPT135 measurements were also performed to differentiate carbon types. From the integration of various proton signals, absolute number average molecular weights $M_n$ can be obtained.

LCST properties ($T_1$) (loss modulus G', storage modulus G", and complex viscosity η of the copolymers as a function of temperature) are determined by rheology (oscillation mode) using a Physica MC 301 (Anton Paar) rheometer. Rheological properties at increasing temperatures were determined using the same polymer concentration as that used in gelling experiments, usually 20 wt %. Viscosity (y-axis, in Pa·s) was plotted versus temperature (x-axis, in ° C.). Although rheological measurements actually determined the onset of gelation shown as an increase of viscosity as a function of temperature, we defined the LCST as the temperature at which the viscosity started to increase.

$T_2$ is determined by heating a gelled composition and visually determine when the thermogelling polymer precipitates.

Intrinsic viscosities are measured using a cone-plate rheometer in rotation mode at various temperatures, using a Physica MC 301 (Anton Paar) rheometer Gelation tests are carried out in 12 mm diameter glass tubes. A copolymer of this invention is dissolved at 20° C. in 10 mM phosphate buffered saline (PBS) at pH 7.4, at a 15 wt % concentration. 1 mL of polymer solution is transferred into a test tube and it is closed with a silicon cap. Then the test tube is placed into a thermostatically controlled water bath at 37° C. After predetermined intervals of time (e.g. 15 min, 30 min and 2 hours), the tube is taken out and turned upside down for 15 seconds. Gelation is considered complete when the polymer solution does not flow at all during 15 seconds. This test is qualitative and used for fast screening of polymers. It does not provide accurate values for LCST and gel mechanical properties.

Degradation time of the B-blocks, the triblock copolymers or materials in general can be assessed in vitro by various analytical techniques including size-exclusion chromatography, nuclear magnetic resonance, MALDI-TOF, high pressure liquid chromatography and combinations of those. The degradation experiments are carried out in 12 mm diameter glass tubes with volume markings. The copolymer is dissolved at 20° C. in 10 mM phosphate buffered saline (PBS) at pH 7.4, and at a 20 wt % concentration. 3.0 mL of solution is poured into each tube to ensure a solid gelation. The glass tubes are placed in a thermostatically controlled bath for 30 minutes to make the 3 mL solutions gel. Then, 7.0 ml of 10 mM PBS at pH 7.4 incubated at the same temperature were placed over the gels. At predetermined time periods, the buffer over the gel was withdrawn and the remaining volume of gel was measured through the volume marking. Then 7.0 mL of fresh buffer pre-incubated at the same temperature were added and the tubes were placed again into the thermostatically controlled bath. The remaining gel volumes were plotted against incubation time to get the degradation profiles. At predetermined amounts of time, pieces of gels can also be removed and analysed by NMR and SEC to calculate the decrease of the number average molecular weight over time.

The invention is explained in detail with the following examples:

EXAMPLE 1

Triblock Polymerization with L-lactide and 1,3-dioxan-2-one

In a 500 mL 2 necks round-bottom flask equipped with magnetic stirring, polyethyleneglycol (50.0 g, 33.3 mmol) was dissolved in 250 mL of dry toluene (<60 μg $H_2O$ per liter) at room temperature. Using a Dean-Stark device with a cooler on top, 150 mL of toluene were distilled off to remove water azeotropically by heating at 140° C. at atmospheric pressure.

After cooling down the solution at 100° C., L-lactide (30.0 g, 208 mmol) and 1,3-dioxan-2-one (30.0 g, 294 mmol) were added at once via the second neck of the flask and 50 mL of dry toluene were added to clean the neck. Using the Dean-Stark device and the cooler again, 50 mL of toluene were distilled off to remove water from the monomers by heating at 140° C. at atmospheric pressure. 100 mL of dry toluene were left in the flask for the polymerization.

After cooling down the mixture at 100° C., Tin(II) 2-ethylhexanoate (0.50 g, ~0.5 wt % versus monomers) was added through the second neck, the Dean-Stark device was removed and the cooler placed directly on top of the flask.

Then the polymerization was done at reflux (120° C.) for a predetermined amount of time (from 16 h to 3 days).

After cooling down at room temperature, the polymer solution was transferred into a one liter round-bottom flask equipped with a powerful magnetic stirring system. 800 mL of dry diethyl ether were slowly added under vigorous stirring (1000 rpm) to make the polymer phase separate as an oil. After 10 minutes of decantation, the top phase (toluene, ether, unreacted monomers, catalyst) was removed by pouring. 20 mL of dry methylene chloride were added to make the polymer less viscous and then 400 mL of dry diethyl ether were added under vigorous stirring (1000 rpm) to wash the polymer. After 10 minutes of decantation, the top phase (methylene chloride, ether and impurities) was removed by pouring it. A second washing with 400 mL of dry diethyl ether after addition of 20 mL dry methylene chloride to the polymer was performed. After decantation, the top phase was removed, and the concentrated polymer was dried at 60° C. under vacuum (20 mbar) for 2 hours in a rotavapor.

Drying of the polymer was completed at room temperature in a drying oven with phosphorous pentoxide at 30° C. and under vacuum (50 m bar) for 3 days.

Then the polymer looked like a colourless transparent paste. The triblock copolymer was characterized by proton nuclear magnetic resonance in deuterated chloroform and size-exclusion chromatography in tetrahydrofuran (double C-column system).

A triblock copolymer of this example had B-blocks comprising 41 mol % L-lactide and 59 mol % 1,3-dioxan-2-one. Each B-block has a number average molecular weight of around 700 Daltons. The number average molecular weight of the polyethylene glycol A-block is around 1500 Daltons. The block ratio therefore is around 1.2.

EXAMPLE 2

Very Hydrophobic Polymer: Triblock Polymerization with L-lactide and 5,5-dimethyl-1,3-dioxan-2-one In a 500 mL 2 necks round-bottom flask equipped with magnetic stirring, polyethyleneglycol (50.0 g, 33.3 mmol) were dissolved in 250 mL of dry toluene (<60 μg $H_2O$ per liter) at room temperature. Using a Dean-Stark device with a cooler on top, 150 mL of toluene were distilled off to remove water azeotropically by heating at 140° C. at atmospheric pressure.

After cooling down the solution at 100° C., L-lactide (25.0 g, 173 mmol) and 5,5-dimethyl-1,3-dioxan-2-one (25.0 g, 192 mmol) were added at once via the second neck of the flask and 50 mL of dry toluene were added to clean the neck. Using the Dean-Stark device and the cooler again, 50 mL of toluene were distilled off to remove water from the monomers by heating at 140° C. at atmospheric pressure. 100 mL of dry toluene were left in the flask for the polymerization.

After cooling down the mixture at 100° C., Tin(II) 2-ethylhexanoate (0.50 g, ~0.5 wt % versus monomers) was added through the second neck, the Dean-Stark device was removed and the cooler placed directly on top of the flask.

Then the polymerization was done at reflux (120° C.) for 3 days.

After cooling down at room temperature, the polymer solution was transferred into a one liter round-bottom flask equipped with a powerful magnetic stirring system. 800 mL of dry diethyl ether were slowly added under vigorous stirring (1000 rpm) to make the polymer phase separate as an oil. After 10 minutes of decantation, the top phase (toluene, ether, unreacted monomers, catalyst) was removed by pouring. 20 mL of dry methylene chloride were added to make the polymer less viscous and then 400 mL of dry diethyl ether were added under vigorous stirring (1000 rpm) to wash the polymer. After 10 minutes of decantation, the top phase (methylene chloride, ether and impurities) was removed by pouring it. A second washing with 400 mL of dry diethyl ether after addition of 20 mL dry methylene chloride to the polymer was performed. After decantation, the top phase was removed, and the concentrated polymer was dried at 60° C. under vacuum (20 mbar) for 2 hours in a rotavapor.

Drying of the polymer was completed at room temperature in a drying oven with phosphorous pentoxide at 30° C. and under vacuum (50 mbar) for 3 days.

Then the polymer looked like a slightly yellow paste. The triblock copolymer was characterized by proton nuclear magnetic resonance in deuterated chloroform and size-exclusion chromatography in tetrahydrofuran (double C-column system).

A triblock copolymer of this example had B-blocks comprising 45 mol % L-lactide and 55 mol % 5,5-dimethyl-1,3-dioxan-2-one. Each B-block had a number average molecular weight of around 750 Daltons. The number average molecular weight of the polyethylene glycol A-block was around 1500 Daltons. The block ratio therefore was around 1.0.

EXAMPLE 3

40 to 50% Modification of the Triblock Copolymer of Example 1 With A) Octanoyl Chloride (Caprylic Acid Derivative) or B) Acetic Anhydride In a 250 mL round-bottom flask equipped with magnetic stirring, the triblock from example 1 (30.0 g) was heated at 60° C. and connected to a high vacuum pump for drying at 0.1 mbar for 2 hours with slow magnetic stirring. After cooling at room temperature, the flask was flushed with nitrogen and then 80 mL dry methylene chloride were added via a syringe, followed by the addition of triethylamine (1.1 equivalent per polymer mole). Then a dropping funnel was mounted above the flask and filled with octanoyl chloride (1.0 equivalent per polymer mole for a maximum of 50% modification) diluted 5 times with dry methylene chloride.

The polymer solution was cooled down at 10° C., stirred at 400 rpm and octanoyl chloride was added in 30 minutes. After addition, the dropping funnel was removed and the flask was flushed with nitrogen again. The cold bath was removed and the reaction was allowed to run at room temperature overnight and followed by nuclear magnetic resonance until the desired degree of modification was achieved.

After reaction, solvents and unreacted triethylamine were removed using a rotavapor (45° C., 20 mbar) for one hour. Then the residue was redissolved using 200 mL of dry ethyl acetate to make the triethylammonium salt precipitate. The precipitate was removed using a glass filter (pore size 4) filled with Celite® filter agent. Then 100 mL ethyl acetate were removed using a rotavapor (40° C., 20 mbar) for 10 minutes.

To the concentrated polymer solution were added 300 mL of dry pentane under vigorous stirring (1000 rpm) to make the polymer phase separate and to remove unreacted octanoyl chloride and caprylic (i.e. octanoic) acid. After decantation, the solvent phase was removed by pouring it out of the flask. 20 mL were added to make the polymer less viscous and then 200 mL of dry pentane were added under vigorous stirring (1000 rpm) to wash the polymer. After decantation and removal of the solvent phase (upper phase), 20 mL were added to make the polymer less viscous and then 200 mL of dry pentane were added under vigorous stirring (1000 rpm) to wash the polymer a second time. After decantation and removal of the solvent phase (upper phase), the concentrated polymer was dried at 50° C. under vacuum (20 mbar) for 2 hours in a rotavapor.

Drying of the polymer was completed at room temperature in a drying oven with phosphorous pentoxide at 30° C. and under vacuum (50 mbar) for 2 days. The modified triblock copolymer was characterized by proton nuclear magnetic resonance in deuterated chloroform and size-exclusion chromatography in tetrahydrofuran (double C-column system).

The procedure for modification with acetic anhydride is different from the procedure described above. However, modification with acetic anhydride is commonly known in the art.

In the case of the example 1 triblock copolymer, 50% modification with octanoyl chloride ($C_8$), example 4A, gave practically the same result in terms of aqueous solubility and gelation as the as a 80% modification with acetic anhydride ($C_2$), example 4B.

EXAMPLE 4

Modification of the Triblock Copolymer of Example 2 With A) Butanoyl Chloride or B) Acetic Anhydride The triblock copolymer of example 2 is modified in a similar way as described in example 4 at 25-30% with acetic anhydride ($C_2$) or butanoyl chloride ($C_4$) to yield a hydrophobic gel with a degradation time, determined of longer than a month.

EXAMPLE 5

Preparation of Paclitaxel-Loaded Micelles

The triblock copolymer from example 1 and Paclitaxel (1:0.4 w/w) were dissolved in acetonitrile and thoroughly mixed. The solvent was evaporated using a stream of nitrogen under stirring. The mixture was re-dissolved in distilled water and a solution with strong opalescence was obtained. After filtration (G3 filter), the solution was lyophilized. Micelles containing Paclitaxel could be smoothly re-dissolved in water and characterized by light-scattering measurements.

EXAMPLE 6

In Vitro Release of Bovine Serum Albumine (BSA) from a Thermogel Followed by UV-Visible Light Spectroscopy The release experiments were carried out in 12 mm diameter glass tubes. The copolymer was dissolved at 20° C. in 10 mM phosphate buffered saline (PBS) at pH 7.4 at a 15 wt % concentration. BSA at a loading of 1 wt % and 5 wt % was dissolved in the same buffer and mixed with the copolymer solution.

The glass tubes were placed in an incubator with a shaking bath at 37° C. or in a water-bath thermostatically controlled at 37° C. for 1 hour. The dimensions of the gel were 20 mm high×12 mm diameter. Then, 2 ml of 10 mM PBS at pH 7.4 or 2 ml incubated at the same temperature were placed over the gels. At predetermined time periods, the buffer over the gel was withdrawn and replaced with a fresh buffer pre-incubated at the same temperature. The withdrawn samples were analyzed by UV-visible light spectroscopy using the absorption at 494 nm for pH 7.4 and the absorption at 458 nm for pH 5.5.

EXAMPLE 7

Use of Thermogels as Temporary Void Filler and Shock Absorber in a Maxillo-Facial Trauma Upon arrival of a patient to the emergency ward, and after diagnosis of a significant maxillo-facial trauma, a biodegradable thermogel would be injected in the damage areas in order to relieve pain (via an analgesic contained in the composition) and act as a shock absorber between broken bone and tissue parts upon gelation. The gel would also prevent unwanted adhesion of damaged tissue and bones to prevent scar tissue formation. This would give the surgeons more time to plan reconstructive surgery and would cause less trauma for the patient during reconstructive surgery because spontaneous healing would be delayed for a few days. By the time the surgeons would be ready, the gel would have started degrading or remaining gel blocks could be removed by cooling them down using cold fluids or instruments and then by sucking the liquefied gel out.

EXAMPLE 8

Injection of a Thermogel Containing Osteogenic and/or Bone Morphogenic Proteins into Intervertebral Discs or Articulate Cartilage to Stop or Reverse Degeneration of Diseased or Damaged Tissues A composition of the thermogel with a LCST of 37° C. containing amongst other components the growth factor TGF-beta-3, or another osteogenic or bone morphogenic protein was prepared. The composition in its liquid form was injected into the intervertebral disc using a small bore needle or a small diameter cannula. Upon reaching LCST, the composition would gel and hold the growth factor in situ over a period of time, releasing it in a slower manner than straight injection of a non-gelling solution.

What is claimed is:

1. A pharmaceutical composition, comprising: an amphiphilic triblock copolymer B-A-B, a medically accepted solvent and an therapeutically active agent, wherein A is a linear poly(ethylene glycol) block having a number average molecular weight ($M_n$) of between 500 and 3000 Daltons, determined with size exclusion chromatography; wherein B are hydrophobic blocks comprising at least two cyclic monomers of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclo-tetradecane-7,14-dione), 1,5-dioxepan-2-one, 6,6-dimethyl-1,4-dioxan-2-one, 2,5-diketomorpholine, pivalolactone, ε-diethylpropiolactone, ethylene carbonate, ethylene oxalate, 3-methyl-1,4-dioxane-2,5-dione, 3,3-diethyl-1,4-dioxan-2,5-dione, 6,8-dioxabicyclooctane-7-one, β-propiolactone, γ-butyrolactone, δ-valerolactone, ε-decalactone, 3-methyl-1,4-dioxane-2,5-dione, 1,4-dioxane-2,5-dione, 2,5-diketo-morpholine, α,α-diethylpropiolactone, γ-butyrolactone, 1,4-dioxepan-2-one, 1,5-dioxepan-2-one, 6,6-dimethyl-dioxepan-2-one, 6,8-dioxabicyclooctane-7-one, or 5,5-dimethyl-1,3-dioxan-2-one, each B-block having a number average molecular weight ($M_n$) of between 400 and 3000 Daltons, determined with size exclusion chromatography; and wherein 25% to 100% of the polymer hydroxyl end-groups are covalently modified with at least one acid chloride, anhydride or isocyanate derivative of a $C_2$-$C_{20}$ fatty acid, and wherein the B-blocks comprise monomer combinations comprising a) between 50 and 100 mol % 5,5-dimethyl-1,3-dioxan-2-one (also called 5,5-dimethyl trimethylene carbonate), b) glycolide and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one, c) lactide and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one, or d) 1,3-dioxan-2-one and at least one monomer that is 5,5-dimethyl-1,3-dioxan-2-one, 1,4-dioxan-2-one, 1,4-dioxepan-2-one, or 1,5-dioxepan-2-one.

2. The pharmaceutical composition according to claim 1, wherein a block ratio, which is defined as a ratio between a sum of the number average molecular weight of the B-blocks and the number average molecular weight of the A-block, ranges between 0.5 and 3.

3. The pharmaceutical composition according to claim 2, wherein the number average molecular weight ($M_n$) of the linear poly(ethylene glycol) block ranges between 900 and 3000 Daltons; wherein the number average molecular weight ($M_n$) of each B-block ranges between 400 and 2000 Daltons; wherein the fatty acids derivatives used to modify the polymer hydroxyl end-groups are derivatives of caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid, or eicosapentaenoic acid; and wherein at least 90% of the polymer hydroxyl end-groups are covalently modified with the at least one acid chloride, anhydride or isocyanate derivative of a $C_2$-$C_{20}$ fatty acid.

4. A pharmaceutical composition according to claim 3, wherein one of the cyclic monomers of the B-blocks is glycolide, lactide, ε-caprolactone or 1,3-dioxan-2-one.

5. A pharmaceutical composition, comprising: an amphiphilic triblock copolymer B-A-B, a medically accepted solvent and an therapeutically active agent, wherein A is a linear poly(ethylene glycol) block having a number average molecular weight ($M_n$) of between 500 and 3000 Daltons, determined with size exclusion chromatography; wherein B are hydrophobic blocks comprising at least two cyclic monomers of glycolide, lactide, ε-caprolactone, p-dioxanone (1,4-dioxan-2-one), trimethylene carbonate (1,3-dioxan-2-one), 1,4-dioxepan-2-one (including its dimer 1,5,8,12-tetraoxacyclo-tetradecane-7,14-dione), 1,5-dioxepan-2-one, 6,6-dimethyl-1,4-dioxan-2-one, 2,5-diketomorpholine, pivalolactone, ε-diethylpropionlactone, ethylene carbonate, ethylene oxalate, 3-methyl-1,4-dioxane-2,5-dione, 3,3-diethyl-1,4-dioxan-2,5-dione, 6,8-dioxabicyclooctane-7-one, β-propiolactone, γ-butyrolactone, δ-valerolactone, ε-decalactone, 3-methyl-1,4-dioxane-2,5-dione, 1,4-dioxane-2,5-dione, 2,5-diketo-morpholine, α,α-diethylpropiolactone, γ-butyrolactone, 1,4-dioxepan-2-one, 1,5-dioxepan-2-one, 6,6-dimethyl-dioxepan-2-one, 6,8-dioxabicycloctane-7-one or 5,5-dimethyl-1,3-dioxan-2-one, each B-block having a number average molecular weight ($M_n$) of between 400 and 3000 Daltons, determined with size exclusion chromatography; and wherein 25% to 100% of the polymer hydroxyl end-groups are covalently modified with at least one acid chloride, anhydride or isocyanate derivative of a $C_2$-$C_{20}$ fatty, acid and wherein the B-blocks comprise monomer combinations a) comprising ε-caprolactone and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one, b) consisting of between 50 and 100 mol % glycolide; and caprolactone as a second monomer, or c) having between 50 and 100 mol % trimethylene carbonate.

6. The pharmaceutical composition according to claim 5, wherein a block ratio, which is defined as a ratio between a sum of the number average molecular weight of the B-blocks and the number average molecular weight of the A-block, ranges between 0.5 and 3.

7. The pharmaceutical composition according to claim 6, wherein the number average molecular weight ($M_n$) of the linear poly(ethylene glycol) block ranges between 900 and 3000 Daltons and the number average molecular weight ($M_n$) of each B-block ranges between 400 and 2000 Daltons; wherein the fatty acids derivatives used to modify the polymer hydroxyl end-groups are derivatives of caproic acid, caprylic acid, capric acid, lauric acid, myristic acid, myristoleic acid, palmitic acid, palmitoleic acid, stearic acid, oleic acid, linoleic acid, alpha-linoleic acid, gamma-linoleic acid, stearidonic acid, rumenic acid, beta-calendic acid, eleostearic acid, puninic acid, parinaric acid, pinolenic acid, arachidic acid, eicosenoic acid, eicosadienoic acid, eicosatrienoic acid, dihomo-gamma-linolenic acid, mead acid, eicosatetraenoic acid, arachidonic acid or eicosapentaenoic acid; and wherein at least 90% of the polymer hydroxyl end-groups are covalently modified with the at least one acid chloride, anhydride or isocyanate derivative of a $C_2$-$C_{20}$ fatty acid.

8. The pharmaceutical composition according to claim 1, wherein the B-blocks comprise the monomer combinations comprising a) between 50 and 100 mol % 5,5-dimethyl-1,3-dioxan-2-one (also called 5,5-dimethyl trimethylene carbonate).

9. The pharmaceutical composition according to claim 1, wherein the B-blocks comprise the monomer combinations comprising the b) glycolide and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one.

10. The pharmaceutical composition according to claim 1, wherein the B-blocks comprise the monomer combinations comprising the c) lactide and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one.

11. The pharmaceutical composition according to claim 1, wherein the B-blocks comprise the monomer combinations comprising the d) 1,3-dioxan-2-one and at least one monomer that is 5,5-dimethyl-1,3-dioxan-2-one, 1,4-dioxan-2-one, 1,4-dioxepan-2-one, or 1,5-dioxepan-2-one.

12. The pharmaceutical composition according to claim 5, wherein the B-blocks comprise the monomer combinations a) comprising ε-caprolactone and at least one monomer that is 1,3-dioxan-2-one, 5,5-dimethyl-1,3-dioxan-2-one, 1,4-dioxan-2-one, 1,4-dioxepan-2-one, or 1,5-dioxepan-2-one.

13. The pharmaceutical composition according to claim 5, wherein the B-blocks comprise the monomer combinations b) consisting of between 50 and 100 mol % glycolide; and caprolactone as a second monomer.

14. The pharmaceutical composition according to claim 5, wherein the B-blocks comprise the monomer combinations c) having between 50 and 100 mol % trimethylene carbonate.

\* \* \* \* \*